United States Patent [19]

Mrozik

[11] 4,174,400

[45] Nov. 13, 1979

[54] ANTHELMINTIC BENZIMIDAZOLES

[75] Inventor: Helmut Mrozik, Matawan, N.J.

[73] Assignee: Merck & Co., Inc., Rahway, N.J.

[21] Appl. No.: 941,997

[22] Filed: Sep. 13, 1978

[51] Int. Cl.$^2$ ............... A61K 31/415; C07D 235/32
[52] U.S. Cl. .................. 424/273 B; 260/578; 260/580; 548/306
[58] Field of Search ............. 548/306; 424/273 B

[56] References Cited

U.S. PATENT DOCUMENTS

| | | | |
|---|---|---|---|
| 3,574,845 | 4/1971 | Actor et al. | 424/273 B |
| 3,929,821 | 12/1975 | Beard et al. | 548/306 |
| 3,929,823 | 12/1975 | Beard et al. | 548/306 |
| 3,929,824 | 12/1975 | Beard et al. | 548/306 |
| 3,993,768 | 11/1976 | Beard et al. | 548/306 |

OTHER PUBLICATIONS

Averkin, et al., J. Med. Chem. 1975, vol. 18, pp. 1164–1166.
Mrozik, et al., J. Med. Chem. 1977, vol. 20, pp. 1225–1227.

*Primary Examiner*—Natalie Trousof
*Attorney, Agent, or Firm*—David L. Rose; Harry E. Westlake

[57] ABSTRACT

Benzimidazole compounds are disclosed which are substituted at the 2-position with a loweralkoxy carbonylamino group and at the 5-position with a halogenated loweralkenyl group or a halogenated loweralkoxy, loweralkylthio, loweralkylsulfinyl or loweralkylsulfonyl. Processes for the preparation of such compounds are disclosed. The compounds are active anthelmintic agents and compositions for such use are also disclosed.

10 Claims, No Drawings

ANTHELMINTIC BENZIMIDAZOLES

BACKGROUND OF THE INVENTION

Benzimidazole anthelmintic compounds have been intensively investigated ever since the discovery of thiabendazole in U.S. Pat. No. 3,017,415. Benzimidazole-2-carbamates containing a trifluoromethyl group on the benzo portion of the molecule group are disclosed in U.S. Pat. No. 3,574,845. Benzimidazole carbamates with an alkoxy, alkylthio, alkylsulfinyl or alkylsulfonyl on the benzo portion are disclosed in U.S. Pat. No. 3,922,824.

SUMMARY OF THE INVENTION

This invention is concerned with benzimidazole carbamates. In particular it is concerned with benzimidazole compounds substituted at the 2-position with a loweralkoxy carbonyl amino group and at the 5-position with a halogenated loweralkenyl group or a halogenated loweralkoxy, loweralkylthio, loweralkylsulfinyl or loweralkylsulfonyl groups. Thus, it is an object of this invention to describe such compounds. It is a further object of this invention to describe processes for the preparation of such compounds. Still further objects are to describe the used of said compounds for the treatment of helminthiasis. Further objects will be apparent from a reading of the following description.

DESCRIPTION OF THE INVENTION

The compounds of the instant invention are best described in the following structural formula:

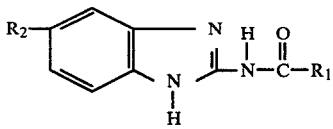

wherein $R_1$ is loweralkoxy; and $R_2$ is halogenated loweralkenyl, halogenated loweralkoxy, halogenated loweralkylthio, halogenated loweralkylsulfinyl, or halogenated loweralkylsulfonyl.

In the instant invention, the term "halogen" or "halo" is intended to include the halogen atoms fluorine, chlorine, bromine or iodine.

The term "loweralkenyl" is intended to include loweralkenyl groups of from 2 to 6 carbon atoms and a single unsaturation such as ethenyl (vinyl), propenyl, butenyl, methyl propenyl and the like.

The term "loweralkyl" is intended to include loweralkyl groups of from 1 to 6 carbon atoms, either branched or straight chain such as methyl, ethyl, propyl, isopropyl, butyl, isobutyl, tert-butyl, pentyl, hexyl and the like.

The term "loweralkoxy" is intended to include those loweralkoxy groups of from 1 to 6 carbon atoms, either branched or straight chain such as, methoxy, ethoxy, propoxy, isopropoxy, butoxy, isobutoxy, tert-butoxy, pentoxy, hexoxy and the like.

The "halogenated loweralkenyl" groups may contain from 1 to 6 halogen atoms which are not necessarily all the same.

The "halogenated loweralkoxy", "halogenated loweralkylthio", "halogenated loweralkylsulfinyl", and "halogenated loweralkylsulfonyl" groups may contain from 1 to 10 halogn atoms which are not necessarily all the same. One aspect of the preferred compounds of this invention are realized in the above structural formula when $R_1$ is methoxy.

The preferred "halogenated loweralkenyl" groups of this invention are trichloroethenyl, 2,3-dichloroethenyl, 1,2-dichloroethenyl, 1,2-difluoro-2-chloro ethenyl, 3,3-dichloro-2-propen-2-yl, and 1,2-dichloro-1-propenyl. Other preferred 5-substituents are 1,1,2-trifluoro-2-chloro ethoxy, 1,1,2-trifluoro-2-chloro ethyl thio.

Specific compounds exemplary of this invention are:
Methyl [5-(trichloroethenyl)-1H-benzimidazole-2-yl] carbamate
Methyl [5-(2,2-dichloroethenyl)-1H-benzimidazole-2-yl] carbamate
Methyl [5-(1,2-dichloroethenyl)-1H-benzimidazole-2-yl] carbamate
Methyl [5-1,2-difluoro-2-chloroethenyl)-1H-benzimidazole-2-yl] carbamate
Methyl [5-(1,1-dichloro-1-prop-2-yl)-1H-benzimidazole-2-yl] carbamate
Methyl[5-(1,2-dichloro-1-propenyl-1H-benzimidazole-2-yl] carbamate The compounds of this invention are prepared according to the following reaction scheme:

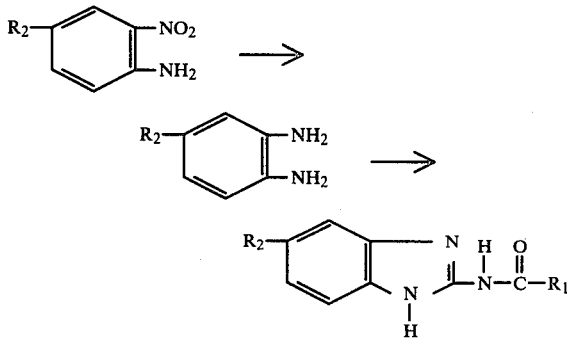

wherein $R_1$ and $R_2$ are as previously defined.

In the foregoing reaction scheme an appropriately substituted O-nitroaniline is reduced to the corresponding O-phenylenediamine. The particular method used to reduce the nitro compound is not critical and many such methods are known in the art. Catalytic hydrogenation using hydrogen either under pressure or at atmospheric pressure in standard laboratory hydrogenation apparatus, using such catalysts as palladium, platinum oxide, and the like is acceptable.

One particularly successful method is to use iron metal and hydrochloric acid in aqueous ethanol. The iron is in a finely divided state, preferably powdered. The reaction is preferably carried out at reflux temperature and is complete in about ½ to 4 hours. In order to moderate the reaction, it is occasionally advisable to add the hydrochloric acid, preferably diluted with ethanol, to the refluxing reaction mixture over a prolonged period of time, such as for the initial period of reaction up to about 1 hour. The product is recovered using techniques known to those skilled in this art.

The O-phenylenediamine is converted to the benzimidazole by treatment with S-methyl-1,3-bis methoxycarbonyl isothiourea in the presence of acetic acid. The reaction is generally carried out in an aqueous organic solvent. Any solvent miscible with water is acceptable. Preferred solvents are alcohols, such as methanol, ethanol; dioxane, tetrahydrofuran, acetonitrile, dimethylformamide and the like. The reaction is generally complete in from 1 to 10 hours at from room temperature to about 150° C. or the reflux temperature of the reaction mixture. The acetic acid is present in the reaction mixture in equimolar amounts, but the quantity of water present is not critical so long as the mixture of solvents is capable of dissolving the starting materials. The product is isolated using techniques known to those skilled in this art.

The $R_2$-substituted nitro aniline starting materials are generally known in the art or procedures for there preparation are known to those skilled in the art.

When the substituted benzimidazole compounds of this invention are employed for the treatment and control of helminthiasis, the specific means employed for administering the compounds to the animal is not critical and any of the methods now used or available for treating animals infected with or susceptible to infection by helminths are satisfactory. Where it is desired to administer the benzimidazole in dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of anthelmintic agent depending upon factors such as the type of host animal to be treated, the severity and type of infection and the weight of the host. For large animals such as sheep, swine and cattle, unit dosages up to 15 gm., containing from 0.1 to 5 gm., of substituted benzimidazole may be employed. It is usually preferred, however, to employ unit dosages weighing from 5 to 10 gm. containing from 0.1 to 2 gm. of benzimidazole. Boluses as well as smaller size tablets contain various binders and lubricants and are compounded by techniques well-known in the art. Capsules are prepared readily by mixing the active ingredient with a diluent such as starch or lactose and filling into the capsule.

In order to treat infected animals by means of a drench, the substituted benzimidazoles of this invention are mixed with a suspending agent such as bentonite and the solid mix is added to water just prior to administration. Preferred drench formulations contain from about 5 to 50% by weight of the benzimidazole.

The compounds described herein also may be administered as a component of the feed of the animals or may be dissolved or suspended in the drinking water. Such compositions comprise the active compound intimately dispersed in an inert carrier or diluent. By inert carrier, is meant one that will not react with the substituted benzimidazole and one that may be administered safely to animals. Preferably, the carrier is one that is, or may be, an ingredient of the animal's ration.

Suitable compositions include feed supplements in which the active ingredient is present in relatively large amounts and which are suitable for addition to the feed either directly or after an intermediate dilution of blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 5 to 50% by weight of the benzimidazole compound are particularly suitable as feed additives.

Such supplements are added to the animal feed in an amount to give the finished feed the concentration of active compound desired for the treatment and control of helminthiasis. Although the desired concentration of active compounds will vary depending upon the factors previously mentioned as well as upon the particular benzimidazole employed, the substituted benzimidazoles of this invention are usually fed at concentrations of between 0.5 to 2.0% in the feed in order to achieve the desired anthelmintic result.

The benzimidazoles of this invention are effective fungicides in a variety of applications. Accordingly, they may be employed as fungicides by conventional techniques in the protection of plants, soils, fruits, seeds, fur, wood, paint, textiles, cosmetics, leather, tobacco, rope, paper, pulp, plastic, fuel, rubber, food and the like.

It should be understood that the substituted benzimidazole compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired. Thus, it will be appreciated that the compounds of this invention may be employed to form fungicidally active compositions containing such compounds as essentially active ingredients thereof, which compositions may also include finely divided dry or liquid diluents, extenders, fillers, conditioners and excipients, including various clays, diatomaceous earth, talc and the like, or water and various organic liquids such as lower alkanols, for example ethanol and isopropanol or kerosene, benzene, toluene and other petroleum distillate fractions or mixtures thereof. The quantity of active compound contained in such formulations will vary widely depending upon the particular benzimidazole compound employed and the particular application intended. In general, useful formulations will contain from about 1 to about 95% of the active compounds.

It should be understood also that the substituted benzimidazoles of the invention may be used in combination one with the other as well as with other fungicidally active materials. For instance, the substituted benzimidazoles disclosed above may be mixed with sorbic acid or its salts, propionic acid or its salts, mycostatin, sodium diacetate, trichomycin, amphotercin, griseofluvin, undecylenic acid, chloroquinadol, 5,7-dichloro8-hydroxyquinoline (Vioform), sodium o-phenylphenate, o-phenylphenol, biphenyl, chlorinated phenols, sodium benzoate, dehydroacetic acid and its salts or esters of parahydroxybenzoic acid, such as the methyl and propyl ester (parabens) to give added fungicidal effect when used in appropriate concentrations. It is quite clear, too, that the compounds of this invention may be used in conjunction with effective anti-bacterial materials in appropriate instances so as to combine the action of each in such a situation as to be particularly useful, for instance, in applications where the presence of bacteria creates undesirable results alongside the detrimental action of fungi. Accordingly, a combination of anti-fungal and anti-bacterial agents will be useful in the preparation of germicidal soaps, in the production of cosmetics, and in food, such as beer, cheese, or meat and other leather applications.

It has been found that growth of various fungi existing in soil is limited or terminated by the addition to the soil of minor quantities of the benzimidazole compounds described. The term soil as used herein is intended to include all media capable of supporting the growth of plants and may include humus, sand, manure, compost, artificially created plant growth solution, and the like. It has been found also that the compounds of the invention are effective against fungal diseases of plants and may be effectively used either by direct contact with the foliage or systemically, by introduction through the roots.

The compounds of this invention also have activity against bacteria and plant nematodes and may, at appropriate levels of concentration, be effectively used to inhibit or prevent the growth of these organisms.

As fungicides, the benzimidazoles of the present invention are useful in inhibiting mold growth in fruit such as citrus fruit. The active agent may be applied at any time before consumption and preferably after harvesting. For instance, the anti-fungal may be applied during initial storage, before or after shipping or during final storage before consumption. The substituted benzimidazoles may be utilized in a number of ways in this regard and may be applied either directly to the fruit in an emulsion, solution, suspension or the like or it may be applied to the fruit container or wrapper. Suitable carriers for the active agents are waxes and other materials presently known in the art.

EXAMPLE 1

1,2-Diamino-4(trichloroethenyl) benzene

A mixture of 10.0 g. (0.037 moles) of 4(trichloroethenyl) o-nitroaniline 10.0 g. (0.18 moles) of iron powder and 350 ml. of 40% aqueous ethanol is stirred vigorously at reflux temperature for 1 hour while 40 ml. (0.008 moles) of 2.0 N hydrochloric acid in 50% aqueous ethanol is added dropwise. The reaction mixture is filtered hot and the solid material washed with ethanol and the filtrate extracted with chloroform. The organic layer is dried with magnesium sulfate and evaporated to dryness in vacuo affording 8.1 g. of 1,2-diamino-4(trichloroethenyl) benzene as a dark brown oil. Thin layer chromatography developed with a 4:1 mixture of benzene and ethyl acetate shows one major spot with an Rf of 0.3. The structure is confirmed with nuclear magnetic resonance and mass spectrometry.

EXAMPLE 2

Methyl[5(trichloroethenyl)-1H-benzimidazole-2-yl] carbamate

Acetic acid (0.133 ml., 0.0023 moles) is added to a stirred mixture of 500 mg. (2.1 mmoles) of 1,2-diamino-4-trichloroethenyl benzene and 452 mg. (2.19 mmoles) of 1,3-bis-(methoxycarbonyl-S-methyl) isothio urea in 12 ml. of 50% aqueous ethanol. The reaction mixture is stirred at reflux for 90 minutes during which time a solid precipitates. The mixture is cooled in ice, filtered and the solid material washed with aqueous ethanol and dried in vacuo affording 580 mg. of methyl[5(trichloroethenyl)-1H-benzimidazole-2yl] carbamate m.p. 235° C. with decomposition. Recrystallization from dimethylformamide/methanol affords an analytical sample with a m.p. of 293°–295° C. with decomposition.

EXAMPLE 3

3-(Dichloroethenyl) aniline

A solution of 32.8 g. (0.125 mole) of triphenylphosphine in 70 ml. of carbon tetrachloride is stirred at 60° C. under a nitrogen atmosphere for 3 hours. A solution of 18.9 g. (0.125 mole) of 3-nitro benzaldehyde in 60 ml. of carbon tetrachloride is added and the reaction mixture stirred for 2 hours at 60° C. and overnight at 25° C. The reaction is filtered and the solids washed repetedly with ether. The filtrate and washings are combined and concentrated in vacuo to an oil. 16 G. of the oil is purified on 500 g. of silica gel eluting with benzene-ether (7:1) 4.76 G. of 3-(2,2-dichloroethenyl) nitrobenzene is recovered.

A mixture of 4.7 g. (0.022 moles) of 3-(2,2-dichloroethenyl) nitrobenzene, 4.7 g. of iron powder and 150 ml. of 50% aqueous ethanol is stirred vigorously under reflux for 30 minutes while 2.5 ml. of 2-normal hydrochloric acid in 50% aqueous ethanol is added dropwise. The mixture is refluxed for an additional 30 minutes. The reaction mixture is filtered and the filtrate made basic with saturated sodium bicarbonate solution. The precipitate is extracted with chloroform and the extracts dried in vacuo affording 4.0 g. of 3-(2,2-dichloroethenyl) aniline as a light oil.

EXAMPLE 4

1,2-Diamino-4-(2,2-dichloroethenyl) Benzene

A mixture of 420 mg. (2.5 mmole) of 3-(2,2-dichloroethenyl) aniline is combined with 2.0 ml. of acetic anhydride and stirred at 35° C. for 1 hour. Fuming nitric acid (90%, d=1.5, 0.2 ml.) is added dropwise over 10 minutes with stirring at 35° C. Stirring is then continued for an additional 90 minutes. The reaction mixture is added to a mixture of 3.0 ml. of water and 2.0 ml. of ethanol and concentrated sulfuric acid (0.75 ml.) is added and the mixture stirred for 2 hours at 35° C. The mixture is cooled in an ice bath and the solid material collected by filtration affording 310 mg. of 5-(2,2-dichloroethenyl) 2-nitro aniline.

The nitro aniline compound (340 mg., 1.46 mmole), iron powder (340 mg.) and 17 ml. of 40% aqueous ethanol (v/v) are stirred vigorously at reflux for 1 hour which 0.2 ml. of 2.0 normal hydrochloric acid in 50% aqueous ethanol is added dropwise. The mixture is filtered hot, the solids washed with ethanol, and the filtrate and washings extracted with chloroform, dried over magnesium sulfate and evaporated to dryness in vacuo affording 250 mg. of a dark brown solid identified as 1,2-diamino-4-(2,2-dichloroethenyl) benzene.

EXAMPLE 5

Methyl[5-(2,2-dichloroethenyl)-1H-benzimidazole-2-yl] carbamate

Acetic acid (0.09 ml., 0.0016 moles) is added to a stirred mixture of 250 mg. (1.24 mmoles) of 1,2 diamino-4(2,2-dichloroethenyl) benzene and 266 mg. (1.29 mmoles) of 1,3-bis(-methoxycarbonyl-S-methyl) isothio urea in 10 ml. of 50% aqueous ethanol. The reaction mixture is heated under reflux for 90 minutes while a solid precipitates. The reaction mixture is cooled, filtered and the solid material washed with ethanol. The residue is evaporated in vacuo affording 350 mg. of methyl[5(2,2-dichloroethenyl)-1H-benzimidazole-2-yl] carbamate m.p. 234°–237° C. Recrystallization from dimethylformamide/water affords a pure sample with a m.p. of 242°–244° C.

EXAMPLE 6

1-Amino 4-(2,2-dichloro-1-methyl ethenyl) Benzene

A mixture of 30.0 g. (0.25 moles) of acetophenone, 196.0 g. (0.75 moles) of triphenylphosphine, and 1120 ml. of carbotetrachloride is stirred in an oil bath at 60° C. for 9 hours. The reaction is allowed to cool to 25° C. and the liquid decanted from the remaining gum. The gum is washed with ether and removed by distilation at atmospheric pressure and the residue distilled affording 35.0 g. of 2-phenyl-1,1-dichloro propene boiling at 119°–120° C.

The distilled material is added dropwise to 33 ml. of concentrated sulfuric acid and 21 ml. of 70% nitric acid at 10°–20° C. with cooling in an ice bath. The ice bath is removed and stirring is continued at 25° C. for 1 hour. The reaction mixture is poured into ice, extracted with ether and concentrated in vacuo. The residue is distilled affording 2 fractions: 7.4 g. b.p. 138°–146° C./1.0 mm. Hg. and 20.9 g. b.p. 147°–153° C./1.0 mm. Hg. The two fractions are identical in gas chromatographic analysis however, and are combined.

The nitro compound is reduced with iron powder (30 g., 0.53 mole) in 50% aqueous ethanol with a catalytic amount of hydrochloric acid. The mixture is refluxed for 40 minutes with vigorous stirring. The reaction is extracted with chloroform and the extracts evaporated to dryness in vacuo, affording 28.5 g. of a colorless oil identified as 1-amino-4-(2,2-dichloro-1-methylethenyl) benzene.

EXAMPLE 7

4-(2,2-Dichloro-1-methylethenyl)-2-nitro aniline 28.5 G. of 1-amino-4-(2,2-dichloro-1-methylethenyl) benzene is treated with 185 ml. of acetic anhydride in 145 ml. of pyridine at 25° C. for 8 hours. The reaction mixture is concentrated to dryness in vacuo and the residue crystallized from ethyl acetate affording 18.0 g. of 1-acetamido-4-(2,2-dichloro-1-methyl ethenyl) benzene, m.p. 165°–166° C.

The acetylated compound (6.0 g.) is dissolved in 120 ml. of acetic anhydride at 50° C. and cooled in an ice bath to 5° C. With stirring a previously prepared mixture of 1.4 ml. of acetic anhydride and 4.3 ml. of concentrated nitric acid at 20° C. is added dropwise over 5 minutes. The mixture is heated to 50° C. for 30 minutes and cooled in an ice bath for 2 hours. The product is filtered, washed with water and dried in vacuo affording 3.1 g. of 1-amino-2-nitro-4-(2,2-dichloro-1-methyl ethenyl) benzene m.p. 142°–143° C. The filtrate is diluted with water (250 ml.) and stirred for 1 hour and filtered affording a further 2.4 g. of product m.p. 139°–141° C.

EXAMPLE 8

1,2-Diamino-4-(2,2-dichloro-1-methylethenyl) benzene

A mixture of 2.1 g. (8.5 mmoles) of 1-amino 2-nitro-4-(2,2-dichloro-1-methylethenyl) benzene 2.1 g. (0.038 moles) of iron powder is suspended in 80 ml. of 40% ethanol and refluxed for 30 minutes. The reaction mixture is filtered while hot, the solid material washed with ethanol and extracted with chloroform and evaporated to dryness in vacuo affording 1.66 g. of a brown glassy substance, which is used as is in the next step.

EXAMPLE 9

Methyl[5(2,2-dichloro-1-methylethenyl)-1H-benzimidazole-2-yl] carbamate 0.54 Ml. (9.4 mmoles) of acetic acid 1.66 g. (7.7 mmoles) of 1,2-diamino 4(2,2-dichloro-1-methylethenyl) benzene and 1.66 g. (8.05 mmoles) of 1,3-bis-(methoxycarbonyl-S-methyl) isothio urea in 60 ml. of 50% aqueous ethanol is reacted as described in Example 5 affording 1.87 g. of methyl[5(2,2-dichloro-1-methylethenyl)-1H-benzimidazole-2-yl] carbamate m.p. 232°–233° C., which thin layer chromatography, on silica gel eluting with chloroform and methanol (19:1), shows as a single spot with an Rf of 0.5.

EXAMPLE 10

3(2-Chloro-1,1,2-trifluoroethylthio) nitrobenzene

A mixture of 50 g. (0.322 moles) of 3-nitrothiophenol, 46.6 g. (0.402 moles) of potassium hydroxide, 60 ml. of acetone and 59 g. (0.395 moles) of 2-chloro-1,1,2-trifluoroethylene is heated in an autoclave with stirring for 1½ hours at 60°–70° C. The reaction mixture is cooled, decanted and the solution evaporated to dryness in vacuo. The oily residue is combined with the solids, water is added and the product extracted with methylene chloride. The extracts are washed with 2.5 N aqueous sodium hydroxide and water, dried and evaporated to dryness in vacuo affording 76.5 g. of 3(2-chloro 1,1,2-trifluoroethylthio nitrobenzene with a b.p. at 0.25 mm. of mercury of 98°–102° C. The structure is verified with nuclear magnetic resonance.

EXAMPLE 11

3(2-Chloro 1,1-2-trifluoroethylthio) aniline

A mixture of 25.0 g. (0.092 moles) of 3(2-chloro 1,1,2-trifluoroethylthio) nitrobenzene, 25 g. (0.045 moles) of iron powder and 450 ml. of 50% aqueous ethanol are combined and treated with 1.44 ml. of concentrated hydrochloric acid as described in Example 8. There is obtained 20.8 g. of crude 3(2-chloro 1,1,2-trifluoroethylthio) aniline as a brown oil which upon distillation in vacuum at 0.3 mm. of mercury at 96°–98° C. affords 13.5 g. of pure 3(2-chloro 1,1,2-trifluoroethylthio) aniline, the structure of which is verified by nuclear magnetic resonance.

EXAMPLE 12

5(2-Chloro 1,1,2-trifluoroethylthio) 2-nitroaniline 9.3 G. (0.041 moles) of 3(2-chloro-1,1,2-trifluoroethylthio) aniline is added to 30 ml. of acetic anhydride over 10 minutes at 20° C. and is stirred for an additional 20 minutes. The reaction mixture is poured onto ice water, stirred for 30 minutes and extracted with methylene chloride. The organic layer is washed with 2.5 N sodium hydroxide and water, dried over magnesium sulfate and evaporated to dryness in vacuo affording 5(2-chloro-1,1,2-trifluoroethylthio)-2-nitro-acetanilide.

This material is dissolved in 150 ml. of acetic anhydride and cooled to 0°–5° C. A mixture of 5.4 ml. of concentrated nitric acid and 1.8 ml. of acetic anhydride is added dropwise over a 15 minute period. The reaction mixture is stirred at room temperature for 4 hours and at 50° C. for 2 hours. The reaction mixture is then poured onto ice water and stirred overnight at 20° C., the aqueous solution is extracted with methylene chloride and the extracts washed with water, dried over magnesium sulfate and evaporated to dryness in vacuo affording 7.8 g. of 5(2-chloro 1,1,2-trifluoroethylthio) 2-nitroacetanilide. The crude material is purified by column chromatography on 250 g. of silica gel eluting with a 4:1 mixture of benzene and ethyl acetate affording 3.0 g. of pure 5(2-chloro 1,1,2-trifluoroethylthio) 2-nitro acetanilide, the structure of which is verified by nuclear magnetic resonance and mass spectrometry. A solution of 1.9 g. (0.006 mole) of 5(2-chloro-1,1,2-trifluoro ethylthio)-2-nitroacetanilide in EtOH (30 ml.) and 30 ml. of concentrated hydrochloric acid is refluxed with stirring for 1 hour. The reaction mixture is cooled and neutralized with 10 N NaOH, then extracted with chloroform, washed with water, dried and concentrated to dryness affording 1.6 g. of 5-(2-chloro-1,1,2-trifluoroethylthio)-2-nitroaniline as a brown oil, identified by infrared analysis. Further chromatographic purification on 45 g. of silica gel eluting with benzene affords 0.66 g. of pure product.

EXAMPLE 13

1,2-Diamino 4(2-chloro 1,1,2-trifluoroethylthio) aniline

A mixture of 460 mg. (1.6 mmoles) of 5-(2-chloro-1,1,2-trifluoroethylthio)-2-nitroaniline is reduced with 460 mg. of iron powder in 20 ml. of 40% aqueous ethanol as described in Example 8 affording 370 mg. of crude 1,2-diamino 4(2-chloro 1,1,2-trifluoroethylthio) benzene which is used without further purification in the following step.

EXAMPLE 14

Methyl [5(2-chloro-1,1,2-trifluoroethylthio)-1H-benzimidazole 2-yl] carbamate 0.05 Ml. of acetic acid is added to a stirred mixture of 190 mg. (743 mmoles) of crude 1,2-diamino 4(2-chloro-1,1,2-trifluoroethylthio) aniline, 161 mg. 1,3-bis-(methoxycarbonyl-S-methyl) isothio urea and 7 ml. of 50% aqueous ethanol and reacted as described in Example 5 affording 85 mg. of methyl [5(2-chloro-1,1,2-trifluoroethylthio)-1H-benzimidazole-2-yl] carbamate m.p. 240°-242° C. after recrystallization from methanol. The structure is verified by mass spectrometry.

What is claimed is:

1. A compound having the formula:

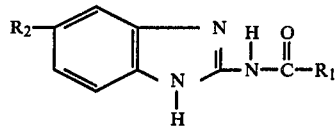

wherein $R_1$ is loweralkoxy; and
$R_2$ is halogenated loweralkenyl.

2. The compound of claim 1 in which $R_1$ is methoxy.

3. The compound of claim 2 wherein the halogenated loweralkenyl is trichloroethenyl, 2,3-dichloroethenyl, 1,2-dichloroethenyl, 1,2-difluoro-2-chloroethenyl, 3,3-dichloro-2-propen-2-yl, or 1,2-dichloro-1-propenyl.

4. The compound of claim 3 which is methyl [5-(trichloroethenyl)-1H-benzimidazole-2-yl] carbamate.

5. The compound of claim 3 which is methyl [5-(2,2-dichloroethenyl)-1H-benzimdazole-2-yl] carbamate.

6. The compound of claim 3 which is methyl [5-(1,2-dichloroethenyl)-1H-benzimidazole-2-yl] carbamate.

7. The compound of claim 3 which is methyl [5-(1,2-difluoro-2-chloroethenyl)-1H-benzimidazole-2-yl] carbamate.

8. The compound of claim 3 which is methyl [5-(1,1-dichloro-1-propen-2-yl)-1H-benzimidazole-2-yl] carbamate.

9. The compound of claim 3 which is methyl [5-(1,2-dichloro-1-propenyl-1H-benzimidazole-2-yl] carbamate.

10. A method for the treatment of helmintic infections which comprises administering to an animal infected with parasites with an effective amount of a compound of claim 1.